United States Patent
Lorbert et al.

(10) Patent No.: US 8,338,141 B2
(45) Date of Patent: Dec. 25, 2012

(54) METHIONINE RECOVERY PROCESSES

(75) Inventors: Steve Lorbert, St. Louis, MO (US);
Jennifer Wu, St. Charles, MO (US);
Farooq Uraizee, Valley Park, MO (US);
Charles Steven Schasteen, St. Louis, MO (US)

(73) Assignee: Novus International, Inc., St. Charles, MO (US)

( * ) Notice: Subject to any disclaimer, the term of this patent is extended or adjusted under 35 U.S.C. 154(b) by 1786 days.

(21) Appl. No.: 10/886,863

(22) Filed: Jul. 8, 2004

(65) Prior Publication Data

US 2005/0089975 A1    Apr. 28, 2005

Related U.S. Application Data

(60) Provisional application No. 60/485,564, filed on Jul. 8, 2003, provisional application No. 60/485,565, filed on Jul. 8, 2003.

(51) Int. Cl.
*C12P 13/12* (2006.01)
*A61K 31/198* (2006.01)

(52) U.S. Cl. .................................. 435/113; 514/562

(58) Field of Classification Search ............. 435/113; 514/562

See application file for complete search history.

(56) References Cited

U.S. PATENT DOCUMENTS

| | | | |
|---|---|---|---|
| 2,471,053 A | 5/1949 | Almquist | |
| 3,139,386 A | 6/1964 | Shigeshi | |
| 3,205,261 A | 9/1965 | Asano et al. | |
| 3,219,543 A | 11/1965 | Douros | |
| 3,729,381 A | 4/1973 | Nakayama | |
| 4,148,688 A * | 4/1979 | Yamada et al. | 435/113 |
| 4,278,765 A | 7/1981 | Debabov | |
| 4,418,688 A | 12/1983 | Loeb | |
| 4,601,893 A | 7/1986 | Cardinal | |
| 4,827,029 A | 5/1989 | Kleemann | |
| 4,837,371 A | 6/1989 | Ogawa | |
| 5,215,897 A | 6/1993 | Sakashita | |
| 5,268,293 A | 12/1993 | Oh | |
| 5,431,933 A | 7/1995 | Binder | |
| 5,463,120 A | 10/1995 | Giraud | |
| 5,622,710 A | 4/1997 | Binder | |
| 5,714,355 A * | 2/1998 | Wagner et al. | 435/106 |
| 5,840,358 A | 11/1998 | Hofler | |
| 5,840,551 A | 11/1998 | Werning | |
| 6,040,160 A | 3/2000 | Kojima | |
| 6,379,934 B1 | 4/2002 | Tilg | |
| 6,656,710 B2 | 12/2003 | Bommarius | |
| 6,673,942 B1 | 1/2004 | Kottenhahn | |
| 2002/0028490 A1 | 3/2002 | Molenaar | |
| 2002/0048793 A1 | 4/2002 | Bathe | |
| 2002/0049305 A1 | 4/2002 | Bathe | |
| 2002/0102664 A1 | 8/2002 | Bathe | |
| 2002/0110877 A1 | 8/2002 | Bathe | |
| 2002/0110878 A1 | 8/2002 | Moeckel | |
| 2002/0142405 A1 | 10/2002 | Tilg | |
| 2003/0045753 A1 | 3/2003 | Ponceblanc | |
| 2003/0049803 A1 | 3/2003 | Rieping | |
| 2003/0054503 A1 | 3/2003 | Rieping | |
| 2003/0059903 A1 | 3/2003 | Rieping | |
| 2003/0092026 A1 | 5/2003 | Rey | |

FOREIGN PATENT DOCUMENTS

| | | |
|---|---|---|
| EP | 0472869 A3 | 7/1991 |
| EP | 0472869 B1 | 7/1991 |
| WO | WO09615246 A1 | 11/1995 |

OTHER PUBLICATIONS

International Search Report of PCT/US04/21756.
CRC Handbook of Chemistry & Physics 51st Ed. 1970-1971, pp. C-741 and C-743.
http://www.formedium.com/USA/amino_acids-and_vitamins:htm#L-Methionine.
Examination Report dated Aug. 27, 2012 (received from Foreign associate on Sep. 6, 2012) from related EP Application No. 04 777 690.1-1521, 5 pages.

* cited by examiner

Primary Examiner — Herbert J Lilling

(57) ABSTRACT

The present invention relates to a method of making a methionine preparation, for example for an animal feed additive. The invention also related to methods for increasing the solubility of a methionine preparation.

10 Claims, 1 Drawing Sheet pK and pI Values at 25°C and Solubility of Amino Acids[a]

| Amino acid | pK₁(COOH)[b] | pK₂(NH₃⁺)[b] | pK₃(NH₃⁺)[b] | pK₄(NH₃⁺) | pI | Solubility, g in 100 g of water | | | |
|---|---|---|---|---|---|---|---|---|---|
| | | | | | | 0°C | 25°C | 50°C | 75°C | 100°C |
| *Divalent* | | | | | | | | | | |
| glycine | 2.34 | 9.60 | | | 5.97 | 14.18 | 24.99 | 39.10 | 54.39 | 67.17 |
| alanine | 2.34 | 9.69 | | | 6.00 | 12.11 | 16.72 | 23.00 | 31.89 | 44.04 |
| L-valine | 2.32 | 9.62 | | | 5.96 | 8.34 | 8.85 | 9.62 | 10.24 | |
| L-leucine | 2.36 | 9.60 | | | 5.98 | 2.27 | 2.33 (35°C) | 2.66 | 3.82 | 5.64 |
| L-isoleucine | 2.26 | 9.62 | | | 5.94 | 3.79 | 4.12 | 4.82 | 6.08 | 8.26 |
| serine | 2.21 | 9.15 | | | 5.68 | 2.20 | 5.02 | 10.34 | 19.21 | 32.24 |
| L-threonine | 2.15 | 9.12 | | | 5.64 | freely soluble in water | | | | |
| L-proline | 1.99 | 10.60 | | | 6.30 | 127.4 | 162.3 | 206.7 | 239.0 (65°C) | |
| L-hydroxyproline | 1.82 | 9.65 | | | 5.74 | 28.86 | 36.11 | 45.18 | 56.67 (65°C) | |
| L-phenylalanine | 1.83 | 9.13 | | | 5.48 | 1.98 | 2.97 | 4.43 | 6.62 | 9.90 |
| L-tryptophan | 2.38 | 9.39 | | | 5.89 | 0.82 | 1.14 | 1.71 | 2.80 | 4.99 |
| DL-methionine | 2.28 | 9.21 | | | 5.74 | 1.82 | 3.38 | 6.07 | 10.52 | 17.60 |
| *Trivalent* | | | | | | | | | | |
| L-aspartic acid | 1.88 | 3.65 (COOH) | 9.60 | | 2.77 | 0.21 | 0.50 | 1.20 | 2.88 | 6.89 |
| L-glutamic acid | 2.19 | 4.25 (COOH) | 9.67 | | 3.22 | 0.34 | 0.84 | 2.19 | 5.53 | 14.00 |
| L-tyrosine | 2.20 | 9.11 | 10.07 (OH) | | 5.66 | 0.02 | 0.05 | 0.11 | 0.24 | 0.57 |
| L-cysteine | 1.71 | 8.33 (?) | 10.78 (?) | | | freely soluble in water | | | | |
| L-histidine | 1.78 | 5.97 (Im)[c] | 8.97 | | 7.47 | | 4.29 | | | |
| L-arginine | 2.18 | 9.09 | 13.2 (Guan)[d] | | 11.15 | the satd aq soln contains 15% (wt/wt), at 21°C | | | | |
| L-lysine | 2.20 | 8.90 | 10.28 | | 9.59 | very freely soluble in water | | | | |
| *Tetravalent* | | | | | | | | | | |
| L-cystine | <1 | 2.1 (COOH) | 8.02 | 8.71 | 5.03 | 0.005 | 0.011 | 0.024 | 0.052 | 0.114 |

[a] Refs. 18–19.
[b] Unless otherwise stated.
[c] Im = imidazoyl group.
[d] Guan = guanidino group.

METHIONINE RECOVERY PROCESSES

RELATED APPLICATIONS

This application claims the benefit of U.S. Provisional Patent Application Ser. No. 60/485,564, filed Jul. 8, 2003, and U.S. Provisional Patent Application Ser. No. 60/485,565, filed Jul. 8, 2003.

FIELD OF THE INVENTION

The present invention relates to an improved method of producing a methionine preparation.

BACKGROUND OF THE INVENTION

Methionine is a sulfur-containing amino acid which is essential in the nutrition of animals, and is often used as a feed additive to animals including poultry, pigs, cows, fish, equine species and even companion animals like dogs and cats. Historically, the methionine used for animal nutrition has been the racemic mixture of D and L methionine. Methionine is unusual in that most animals can utilize both the D and L forms of the amino acid. For all other essential amino acids, only the L form of the amino acid has nutritive value. Some specific animal studies have been completed which show benefits for feeding L-methionine as opposed to the racemic mixture. Faster absorption and better utilization in the muscle has been shown for some species under some selected feeding conditions. There are some specific applications outside of animal nutrition where the use of L-methionine is preferred. For example, L-methionine has known uses in human medicine and in the pharmaceutical industry. It is useful as a lipotropic agent and for the treatment of liver disease in animals. L-methionine and L-methionine derivatives are required for manufacturing therapeutic peptides, which are synthesized from single amino acids. Unfortunately, the production of the single isomer, L-methionine, is much more difficult and expensive as compared to producing the racemic mixture. Therefore, it would be very beneficial to establish a relatively inexpensive, industrial process for the production of L-methionine for human healthcare which also could be used for animal nutrition.

Several methods have been available for the production of L-methionine. For example, there is a process for the production of L-methionine by optically resolving DL-methionine prepared by a synthetic method (Pokorny et al., 1970, Phytochemistry 9:2175). Commercial production of L-methionine using acylase catalyzed cleavage of N-acetyl-D,L methionine is well known (see, for example, U.S. Pat. No. 4,827,029 and U.S. Pat. No. 6,656,710). These processes are fairly complex and therefore add significant additional cost in separating L-methionine from the racemic mixture. Processes based on selective crystallization are also known (see U.S. Pat. No. 6,673,942). It is also known to produce L-methionine by hydrolyzing proteins. Additionally, it is known to produce L-methionine by a microbiological process (e.g., fermentation).

There has been much published regarding the development of bacterial and yeast strains for L-methionine production. It is well known that L-methionine synthesis is tightly regulated in microorganisms. Consequently, the productivity of these microorganisms has been low with respect to methionine production. Kase and Nakayama isolated *Coryneform* mutants capable of producing 2 g methionine/liter (Agr Biol. Chem., 39(1), 153-160, 1975). Gomes and coworkers have also used classical mutagenesis techniques to isolate methionine analog resistant mutants of *Corynebacterium lilium*. Production of methionine by their isolate was shown to be much improved over the wild type starting strain, but much below commercial titres typically seen for other amino acids like lysine which is produced by fermentation. Commercial lysine fermentations typically reach titres approaching 100 g lysine/liter (see U.S. Pat. No. 5,268,293).

More recently, it has been reported by Moeckel, et al. in U.S. patent application No. 2002/0110878 that L-methionine production can be improved dramatically through the amplification of key genes in the methionine pathway. The expression of native *Coryneform* metA and metY genes was improved through the use of a specially constructed plasmid system. Shake flask fermentations of this strain reached a final methionine concentration of 16.0 grams of methionine/ liter (g/L). Modification of other genes in the pathway in combination with the improvements in metA and metY should result in strains with even higher productivities. Using larger commercial fermentation systems which can support higher cell densities, these highly productive methionine-producing strains should be capable of producing methionine at high titre. Development of high methionine producing strains of *E. coli* is also being investigated. (See JP2000-139471 and 157267).

Because of the low solubility of methionine under normal fermentation conditions, its separation from whole cells and other fermentation broth component is a major issue which needs to be solved to be able to produce L-methionine economically. Typically, a neutral pH is preferred for the production of L-amino acids. For example, U.S. Pat. No. 3,729,381 teaches that a neutral pH is preferred to obtain high yield of L-methionine by fermentation (e.g., claim 3, and column 3, lines 28-31). U.S. Pat. No. 5,840,551 also teaches a method of producing L-amino acids by fermentation using neutral pH (e.g., see Example 1). The preferred fermentation temperature for organisms like *Corynebacteria* and *E. coli* is in the range of 30-37° C. Because of L-methionine's low solubility, both soluble and insoluble methionine fractions would exist in the broth. An effective separations process is needed to produce purified L-methionine from fermentation broth.

SUMMARY OF THE INVENTION

The present invention provides methods for recovering purified L-methionine from fermentation broth. The purification strategies rely on methods for increasing the solubility of an L-methionine preparation, so that the it can subsequently be separated from whole cells and other fermentation broth solids. The L-methionine which has been solubilized can then be selectively crystallized to separate it from the more soluble components in the fermentation broth. Methionine solubility is manipulated to make a purified methionine end product which can be dried and granulated for use in the animal feed sector.

The methods of the present invention, which include methods comprising adjusting the pH of the methionine to an acidic or basic pH, and/or increasing the temperature of the methionine preparation to at least 40° C., are useful for increasing the recovery of L-methionine. L-methionine has limited aqueous solubility, resulting in loss of significant amounts as insoluble material from high methionine titre fermentation broths. The present invention provides simple, cost-effective methods for maximizing the recovery of L-methionine in making a methionine preparation from a fermentation broth.

In one aspect, the invention provides a method of increasing the solubility of a methionine preparation comprising adding an acid or a base into the methionine preparation. If an acid is added, sulfuric acid, hydrochloric acid, phosphoric acid, nitric acid or 2-hydroxy-4-(methylthio)butanoic acid can be used. In one embodiment, adding the acid decreases the pH of the methionine preparation to between pH 1.5-3. Alternatively, ammonium hydroxide, sodium hydroxide or potassium hydroxide can be used as the base in the method. In one embodiment, adding the base increases the pH of the methionine preparation to a pH 8.5 or above.

The method according to this aspect can further comprise increasing the temperature to at least 40° C. The temperature can be further increased to at least 50° C., typically at least 60° C. or preferably at least 70° C.

In another aspect, the invention provides a method of increasing the solubility of a methionine preparation comprising increasing temperature of the methionine preparation to at least 40° C. The temperature can also be increased to at least 50° C., typically at least 60° C. In one embodiment, the temperature is increased to at least 70° C.

The method according to this aspect can further comprise adding an acid or base to the methionine preparation. The acid can be sulfuric acid, hydrochloric acid, phosphoric acid, nitric acid or 2-hydroxy-4-(methylthio)butanoic acid. In one embodiment, adding the acid decreases the pH of the methionine preparation to between pH 1.5-3. The base can be ammonium hydroxide, sodium hydroxide or potassium hydroxide. In one embodiment, adding the base increases the pH of the methionine preparation to a pH above pH 8.5.

In another aspect of this invention, a method of making a methionine preparation is provided, comprising the following steps:
(a) culturing a methionine-producing microorganism in a fermentation medium to yield a fermentation broth;
(b) solubilizing methionine in the fermentation broth by addition of an acid to lower the pH to 3.5 or below, or a base to raise the pH to 8.5 or above;
(c) removing insoluble material from the fermentation broth to yield a clarified broth;
(d) crystallizing methionine from the clarified broth; and,
(e) isolating the methionine crystals to produce a methionine preparation.

According to one embodiment, the temperature of the fermentation broth can be raised to further increase the solubility of methionine prior to removal of the insoluble material. In one embodiment, the temperature is raised to at least 40° C. In another embodiment, the temperature is raised to at least 50° C. In a preferred embodiment, the temperature is raised to at least 60° C. In a most preferred embodiment, the temperature is raised to at least 70° C.

If an acid is added, sulfuric acid, hydrochloric acid, phosphoric acid, nitric acid or 2-hydroxy-4-(methylthio)butanoic acid can be used. Alternatively, ammonium hydroxide, sodium hydroxide or potassium hydroxide can be used as the base in the method.

The insoluble material can be removed from the fermentation broth by filtration or centrifugation. Upon removal of insoluble material, the clarified broth can optionally be concentrated. Once removed of insoluble material, the methionine in the clarified broth can be crystallized by reducing the temperature to below 10° C., preferably at or below 4° C., and by adjusting the pH to between pH 5.5 and 6. The methionine preparation can be dried and optionally granulated for use.

In still another aspect, the invention provides for a method of making a methionine preparation comprising:
(a) culturing a methionine-producing microorganism in a fermentation medium to yield a fermentation broth;
(b) solubilizing methionine in the fermentation broth by raising the temperature of the broth to at least 40° C.;
(c) removing insoluble material from the fermentation broth to yield a methionine-enriched clarified broth;
(d) crystallizing methionine from the clarified broth; and,
(e) isolating the methionine crystals to produce a methionine preparation.

In one embodiment, the temperature of broth is raised to at least 50° C. In another embodiment, the temperature is raised to at least 60° C. In still another embodiment, the temperature is raised to at least 70° C.

To further solubilize methionine, the method can further comprise raising the pH of the broth to at least 8.5, or lowering the pH to 3.5 or below. The pH can be lowered by addition of an acid. In one embodiment, the acid can be selected from the group consisting of 2-hydroxy-4-(methylthio)butanoic acid, hydrochloric acid, sulfuric acid, phosphoric acid and nitric acid. Alternatively, the pH can be raised to at least 8.5 by addition of a base. The base can be selected from the group consisting of ammonium hydroxide, sodium hydroxide and potassium hydroxide.

The clarified broth produced in this aspect can be further dried to yield a dried methionine preparation.

In another aspect, the invention provides for a method of making a methionine preparation comprising:
(a) culturing a methionine-producing microorganism in a fermentation medium to produce a fermentation broth;
(b) separating methionine-enriched insoluble material from the fermentation broth;
(c) solubilizing methionine from the methionine-enriched insoluble material by addition of an acid to lower the pH to 3.5 or below, or a base to raise the pH to 8.5 or above to produce a methionine-enriched broth;
(d) removing insoluble material to yield a methionine-enriched clarified broth;
(e) optionally combining the methionine-enriched clarified broth from step d with the soluble methionine fraction from step b; and,
(e) crystallizing methionine from the methionine-enriched fractions; and,
(f) isolating the methionine crystals to produce a methionine preparation.

The insoluble material can be collected by centrifugation or filtration. Once collected, the insoluble material can be resuspended in solution before addition of an acid or base. According to one embodiment, the temperature can be raised to at least 40° C. in order to further increase the solubility of methionine. In another embodiment, the temperature is raised to at least 50° C. In a preferred embodiment, the temperature is raised to at least 60° C. In a most preferred embodiment, the temperature is raised to at least 70° C.

If an acid is added, sulfuric acid, hydrochloric acid, phosphoric acid, nitric acid or 2-hydroxy-4-(methylthio)butanoic acid can be used. Alternatively, ammonium hydroxide, sodium hydroxide or potassium hydroxide can be used as the base in the method.

Once the methionine has been solubilized, the remaining insoluble material can be removed by filtration or centrifugation. Upon removal of insoluble material, the clarified broth can be concentrated. Once removed of insoluble material, methionine can be purified from the clarified broth by crystallization. Crystallization can be performed by reducing the temperature to below 10° C., preferably at or below 4° C., and by adjusting the pH to between pH 5.5 and 6. The methionine preparation can be dried and optionally granulated for use.

In still another aspect, the invention provides a method of making a methionine preparation comprising the following steps:
a) culturing a methionine-producing microorganism in a fermentation medium, wherein the pH of the fermentation medium is adjusted to an acidic pH or basic pH;
b) obtaining a methionine-containing fermentation broth from the culturing; and
c) concentrating the methionine-containing fermentation broth to produce a methionine preparation.

The pH can be adjusted to between pH 1.5 and pH 3. In a particular embodiment, the pH is adjusted by adding sulfuric acid, hydrochloric acid, phosphoric acid, nitric acid or 2-hydroxy-4-(methylthio)butanoic acid. Alternatively, the pH can be adjusted to 8.5 or above. Ammonium hydroxide, sodium hydroxide or potassium hydroxide can be added to adjust the pH.

The method according to this aspect can further comprise adding 2-hydroxy-4-)methylthio)butanoic acid to the fermentation medium and/or to the fermentation broth.

The fermentation broth can be further dried to obtain an animal feed additive in the desired powder or granule form. The methionine preparation can also be further dried to obtain a dried methionine preparation.

In one embodiment, the pH of the methionine preparation is adjusted to between pH 7.5-12 before drying. Alternatively, the pH of the methionine preparation is adjusted to pH 9-11 before drying. Ammonium stripping and recrystallization can additionally be performed in this method.

The pH of the methionine preparation can additionally be adjusted to between pH 2.5-7 before drying. In another embodiment, the pH of the methionine preparation is adjusted to pH 4-7 before drying. In yet another embodiment, the pH of the methionine preparation is adjusted to between pH 5-7 before drying.

In another aspect, the invention provides a method of making a methionine preparation comprising the following steps:
a) culturing a methionine-producing microorganism in a fermentation medium, wherein the pH of the fermentation medium is adjusted;
b) obtaining a methionine-containing fermentation broth from the culturing; and
c) removing biomass from the methionine-containing fermentation broth to produce a methionine preparation.

The pH can be adjusted to between pH 1.5 and pH 3. In a particular embodiment, the pH is adjusted by adding sulfuric acid, hydrochloric acid, phosphoric acid, nitric acid or 2-hydroxy-4-(methylthio)butanoic acid. Alternatively, the pH can be adjusted to between pH 8 and pH 10. Ammonium hydroxide, sodium hydroxide or potassium hydroxide can be added to adjust the pH.

The method according to this aspect can further comprise adding 2-hydroxy-4-methylthiobutanoc acid to the fermentation medium and/or to the fermentation broth.

In yet another embodiment, the method further comprises drying the fermentation broth to obtain an animal feed additive in the desired powder or granule form. The methionine preparation can be further dried to obtain a dried methionine preparation.

The pH of the methionine preparation can be further adjusted to between pH 7.5-12 before drying. In one embodiment, the pH of the methionine preparation is adjusted to between pH 9-11 before drying. In another embodiment, the method further comprises ammonium stripping and crystallization before drying.

Alternatively, the pH of the methionine preparation can be adjusted to pH between 2.5-7 before drying. In one embodiment, the pH of the methionine preparation is adjusted to between pH 4-7 before drying. In another embodiment, the pH of the methionine preparation is adjusted to between pH 5-7 before drying.

In another aspect, the invention provides a method of making a methionine preparation comprising the following steps:
a) culturing a methionine-producing microorganism in a fermentation medium;
b) obtaining a methionine-containing fermentation broth from the culturing, wherein the pH of the fermentation broth is adjusted; and
c) concentrating the methionine-containing fermentation broth to produce a methionine preparation.

The pH can be adjusted to between pH 1.5 and pH 3. In a particular embodiment, the pH is adjusted by adding sulfuric acid, hydrochloric acid, phosphoric acid, nitric acid or 2-hydroxy-4-(methylthio)butanoic acid. Alternatively, the pH can be adjusted to between pH 8 and pH 10. Ammonium hydroxide, sodium hydroxide or potassium hydroxide can be added to adjust the pH.

2-hydroxy-4-(methylthio)butanoic acid can be added to the fermentation medium and/or to the fermentation broth.

In yet another embodiment, the method further comprises drying the fermentation broth to obtain an animal feed additive in the desired powder or granule form. The methionine preparation can be further dried to obtain a dried methionine preparation.

The pH of the methionine preparation can be adjusted to between pH 7.5-12 before drying. In one embodiment, the pH of the methionine preparation is adjusted to between pH 9-11 before drying.

In still another embodiment, the method further comprises ammonium stripping and crystallization before drying.

Alternatively, the pH of the methionine preparation can be adjusted to between pH 2.5-7 before drying. In one embodiment, the pH of the methionine preparation is adjusted to between pH 4-7 before drying. In another embodiment, the pH of the methionine preparation is adjusted to between pH 5-7 before drying.

In yet another aspect, the invention provides a method of making a methionine preparation comprising the following steps:
a) culturing a methionine-producing microorganism in a fermentation medium;
b) obtaining a methionine-containing fermentation broth from the culturing, wherein the pH of the fermentation broth is adjusted; and
c) removing from the methionine-containing fermentation broth to produce a methionine preparation.

In one embodiment, the method further comprises adding 2-hydroxy-4-(methylthio)butanoic acid to the fermentation medium. Alternatively, 2-hydroxy-4-(methylthio)butanoic acid can be added to the fermentation broth.

In one embodiment, the pH is adjusted to between pH 1.5 and pH 3. The pH can be adjusted by adding sulfuric acid, hydrochloric acid, phosphoric acid, nitric acid or 2-hydroxy-4-(methylthio)butanoic acid.

In another embodiment, the pH is adjusted to between pH 8 and pH 10. The pH can be adjusted by adding ammonium hydroxide, sodium hydroxide or potassium hydroxide.

In yet another aspect, the invention provides for a method of producing a feed additive, comprising:
(a) culturing a methionine-producing microorganism in a fermentation medium to produce a fermentation broth; and,
(b) drying the fermentation broth to obtain an animal feed additive in the desired powder or granule form.

The methionine preparation can be further dried to obtain a dried methionine preparation.

The pH of the methionine preparation can be adjusted to between pH 7.5-12 before drying. In one embodiment, the pH of the methionine preparation is adjusted to between pH 9-11 before drying. The method can further comprise ammonium stripping and crystallization before drying.

Alternatively, the pH of the methionine preparation can be adjusted to between pH 2.5-7 before drying. In one embodiment, the pH of the methionine preparation is adjusted to between pH 4-7 before drying. In another embodiment, the pH of the methionine preparation is adjusted to between pH 5-7 before drying.

In another aspect, the invention provides an acidified fermentation broth comprising methionine. The acidified fermentation broth has a pH of 1 to 5, typically a pH of between 1 to 4. In another embodiment, the acidified fermentation broth has a pH of 1 to 3. In a particular embodiment, the acidified fermentation broth has a pH of 1.5 to 3. The acidified fermentation broth can further comprise 2-hydroxy-4-(methylthio)butanoic acid.

BRIEF DESCRIPTION OF DRAWINGS

FIG. 1 is a table showing the solubility of various amino acids.

DETAILED DESCRIPTION OF THE INVENTION

DEFINITIONS

The term "amino acid preparation" refers to a preparation of L-amino acids including L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine, and the salts thereof (such as methionine hydrochloride or methionine sulfate). An "amino acid preparation", according to the present invention, can be made by any known methods in the art and as described herein, preferably by fermentation of an amino acid producing microorganism. An "amino acid preparation" of the present invention can be in any liquid or dry forms known in the art, and it can be a purified amino acid or the salt thereof (i.e., at least 95% by weight), or it can contain less than 95% by weight of amino acid or the salt thereof, but also contain other components (e.g., culture broth, and/or whole bacteria cells) in addition to the amino acid. An "amino acid preparation", according to the present invention, can also contain two or more amino acids and the salts thereof. Preferably, the "amino acid preparation" is in a form that can be used as an animal feed supplement.

The term "methionine preparation" refers to an amino acid preparation containing a methionine. A "methionine preparation" can be prepared by any known methods in the art and as described herein, preferably by fermentation of a methionine-producing microorganism. A "methionine preparation" of the present invention can be in any liquid or dry forms known in the art, and it can be a purified methionine or the salt thereof (i.e., at least 95% methionine by weight), or it can contain less than 95% by weight of methionine or the salt thereof, but also contain other components (e.g., culture broth, and/or whole bacteria cells) in addition to methionine. A "methionine preparation", according to the present invention, can also contain methionine and one or more other amino acids and their salts thereof. Preferably, the "methionine preparation" is in a form that can be used as an animal feed supplement.

The term "purified amino acid preparation", as used herein, refers to one form of the amino acid preparation as define herein above which has an amino acid content (% per weight) of at least 90%, for example, 92%, 94%, 96%, 98%, or 100%.

The term "dried amino acid preparation", as used herein, refers to one form of the amino acid preparation as defined herein above which has a water content (% per weight) of at most 10%, e.g., 8%, 6%, 4%, 2%, 1% or 0%.

The term "purified methionine preparation", as used herein, refers to one form of the methionine preparation as define herein above which has a methionine content (% per weight) of at least 90%, for example, 92%, 94%, 96%, 98%, or 100%.

The term "dried methionine preparation", as used herein, refers to one form of the methionine preparation as defined herein above which has a water content (% per weight) of less than 10%, e.g., 8%, 6%, 4%, 2%, 1% or 0%.

The term "solubility", as used herein, refers to the solid/liquid solubility, i.e., the ability or tendency of an amino acid to blend uniformly with a liquid, e.g., water. Solids vary from 0-100% in their degree of solubility in liquids, depending on the chemical nature of the substances; to the extent that they are soluble, they lose their crystalline form and become molecularly or ionically dispersed in the solvent to form a true solution. The "solubility of a methionine preparation" and "solubility of methionine in a methionine preparation", as used herein, refer to the aqueous solubility of methionine, e.g., in water, expressed as g/L. For example, DL-methionine has a water solubility of 33.81 g/L at 25° C. according to Merck Index, $12^{th}$ Edition, 1996.

The term "increasing the solubility" refers to the increase of aqueous soluble amino acid concentration by pH adjustment as compared to the concentration of aqueous soluble methionine before adjusting the temperature and/or pH. There is an "increase" in solubility when the solubility of an amino acid is at least 20% greater (e.g., 21%, 25%, 30%, 40%, 50%, 60%, 70%, 80%, 90%, 100%, 200%, 300%, 400%, 500% greater, or more, than its solubility at pH 7.0 at the same temperature. For example, if a methionine preparation has a water soluble methionine concentration of 33.81 g/L at 25° C. at pH 7.0. It is said that there is an increase in the solubility of such methionine preparation if, by adjusting the pH and/or temperature, the methionine preparation has a water soluble methionine concentration of at least 40.57 g/L, e.g., at least 47.33 g/L, 50.72 g/L, 54.10 g/L, 57.48 g/L, 60.86 g/L, 64.24 g/L, 67.62 g/L, 101.43 g/L, 135.24 g/L, 169.05 g/L or more. The water soluble concentration of amino acid can be measured by any methods for solubility determination known in the art, e.g., as described in Daniels e al. 1970, Experimental Physical Chemistry, $7^{th}$ ed., New York: McGraw-Hill; Halpern, A. M. and Reeves, H. I., 1988, Experimental Physical Chemistry, A laboratory Textbook, Scott Foreman and Company; Showmaker et al., 1981, Experiments in Physical Chemistry, $4^{th}$ ed., New York: McGraw-Hill.

The term "base", as used herein, refers to any substance which can alter the pH of a solution from a neutral pH of 7.0 to a basic pH (i.e., 7.1 to 14). Typically, a base is a substance of a large class of compounds with one or more of the following properties: bitter taste, slippery feeling in solution, ability to turn litmus blue and to cause other indicators to take on characteristic colors, ability to react with (neutralize) acids to form salts. Included are both hydroxides and oxides of metals. Water-soluble hydroxides such as sodium, potassium, and ammonium hydroxide undergo ionization to produce hydroxyl ion ($OH^+$) in considerable concentration, and it is this ion that causes the previously mentioned properties common to bases. Such a base is strong or weak according to the fraction of the molecules that breaks down (ionizes) into positive ion and hydroxyl ion in the solution. Base strength in solution is expressed by pH. Common strong bases (alkalis) are sodium and potassium hydroxides, ammonium hydroxide, etc. These are caustic and corrosive to skin, eyes, and mucous membranes. The pH range of basic solutions is from 7.1 to 14. Modern chemical terminology defines bases in a broader manner. A Lowry-Bronsted base in any molecular or ionic substance that can combine with a proton (hydrogen ion) to form a new compound. A Lewis base is any substance that provides a pair of electrons for a covalent bond with a Lewis acid. Examples of such bases are hydroxyl ion and most anions, metal oxides, and compounds of oxygen, nitrogen, and sulfur with non-bonded electron pairs (such as water, ammonia, and hydrogen sulfide).

The term "acid", as used herein, refers to any substance which can alter the pH of a solution from a neutral pH of 7.0 to an acidic pH (i.e., 6.9 to 1). Typically, an acid is a substance of a large class of chemical substances whose water solutions have one or more of the following properties: sour taste, ability to make litmus dye turn red and to cause other indicator dyes to change to characteristic colors, ability to react with and dissolve certain metals to form salts, and ability to react with bases or alkalis to form salts. All acids contain hydrogen. In water, ionization or splitting of the molecule occurs so that some or most of this hydrogen forms $H_3O^+$ ions (hydronium ions), usually written more simply as $H^+$ (hydrogen ion). Acids are referred to as strong or weak according to the concentration of $H^+$ ion that results from ionization. Hydrochloric, nitric, and sulfuric are strong or highly ionized acids; acetic acid ($CH_3COOH$) and carbonic acid ($H_2CO_3$) are weak acids. Tenth normal hydrochloric acid is 100 times as acid (pH=1) as tenth normal acetic acid (pH=3). The pH range of acids is from 6.9 to 1. The hydroxy analog of methionine (e.g., 2-hydroxy-4-(methylthio)butanoic acid is an "acid" under the definition of the present invention.

The present invention is based on the unexpected discovery that the solubility of a methionine preparation can be increased by adjusting the pH during the preparation process to a basic or acidic pH. The present invention is also based on the discovery that solubility of methionine in a fermentation broth can be dramatically increased by increasing the temperature to at least 40° C.

The present invention can be used in combination with any known method of producing methionine preparation, e.g., high purity methionine or fermentation broth containing methionine. The present invention can be used for methionine preparation by fermentation, for example, as described in U.S. Pat. Nos. 3,729,381, 5,840,551, 6,379,934; 5,431,933; 5,622,710; 5,840,358; or by optical resolution of DL-amino acids prepared in an organic synthetic-chemical method; or by chemico-enzymatic processes as described in U.S. Pat. No. 5,215,897; Japanese Patent Publication Nos. 22380/66, 2274/79, 18867/82, Japanese Patent Application Kokai (Laid-Open) No. 140890/84), the entirety of each is hereby incorporated by reference.

A preferred method of producing a methionine preparation, according to the present invention, is by fermentation of a methionine-producing microorganism. It should be understood, however, the pH adjustment as taught in the present invention can readily be applied to other methods of preparing a methionine preparation, e.g., by chemical synthesis and protein hydrolysis, so long as the pH as adjusted does not interfere with the production of methionine by such method. In addition, the pH adjustment as taught in the present invention can also be used to increase the solubility of other amino acid preparation, in particular, for other amino acid with low solubility problems, e.g., leucine, isoleucine, serine, glutamic acid, aspartic acid, some aromatic ring-containing amino acids such as tryptophan, tyrosine, phenylalanine, other sulfur-containing amino acids such as cysteine.

The present invention provides a method of making a methionine preparation by fermentation of a methionine-producing microorganism. The adjustment of pH can occur at any step of the process of making such a methionine preparation so long as it does not interfere with the fermentation process and the production of methionine by the methionine-producing microorganism. Likewise, the increase in temperature can occur at any stage of the process, so long as it does not interfere with the fermentation process and the production of methionine by the methionine-producing microorganism.

In one embodiment, the method of making such a methionine preparation comprises a) culturing a methionine-producing microorganism in a fermentation medium, where the pH of the fermentation medium is adjusted to an acidic or basic pH; b) obtaining a methionine-containing fermentation broth from said the culturing; and c) concentrating the methionine-containing fermentation broth to produce a methionine preparation.

In another embodiment, the method of making a methionine preparation comprises a) culturing a methionine-producing microorganism in a fermentation medium; b) obtaining a methionine-containing fermentation broth from said the culturing, where the pH of the fermentation broth is adjusted to an acidic or basic pH; and c) concentrating said the methionine-containing fermentation broth to produce a methionine preparation.

In addition to adjusting the pH to an acidic or basic pH in the aforementioned embodiments, the solubility of methionine can be further increased by increasing the temperature of the fermentation medium or fermentation broth to at least 40° C.

In yet another embodiment, the method of making such a methionine preparation comprises a) culturing a methionine-producing microorganism in a fermentation medium; b) increasing the temperature of the fermentation medium to at least 40° C.; c) obtaining a methionine-containing fermentation broth from the culturing; and d) concentrating the methionine-containing fermentation broth to produce a methionine preparation.

In addition to providing the primary means of separating the methionine from the whole cells, lowering or raising pH in combination with temperature will aid in inactivating the cells. Whole cell inactivation is usually performed in conjunction with removing the cells from the broth. The inactivated cells can be used as an animal feed supplement, or are disposed of in waste treatment operations.

Microorganism

Any microorganism can be effectively used in this invention on the sole condition that it should be able to produce an amino acid, e.g., methionine. The microorganisms to which the present invention relates can prepare amino acids from glucose, sucrose, lactose, fructose, maltose, molasses, starch, cellulose or from glycerol, ethanol, and other carbohydrates.

Examples of useful methionine producing bacteria include, but are not limited to, those described in U.S. patent application Nos. 2003/0,092,026A1; 2003/0,059,903A1; 2003/0,054,503A1; 2003/0,049,803A1; 2002/0,142,405A1; 2002/0,110,878A1; 2002/0,110,877A1; 2002/0,102,664A1; 2002/0,049,305A1; 2002/0,048,793A1; 2002/0,028,490A1; and U.S. Pat. Nos. 6,379,934B1; 6,040,160; 3,219,543; 3,729,381; 3,756,916; 3,139,386, each of the patents and patent applications is hereby incorporated in its entirety.

Most of the useful bacteria for the present invention are classified as *Corynebacterium, Brevibacterium, Arthrobacter* or *Microbacterium*. All of the genera are found within the class Schizomycetes. *Brevibacterium* is a genus within the family Brevibacteriaceae, order Eubacteriales and is generally characterized by: short, unbranching rods; generally non-motile; type of motility of motile species is peritrichous or uncertain; sometimes chromogenic, with non-water soluble reddish, reddish orange, yellow or brown pigments; may or may not reduce nitrates; glucose broth usually becomes acid; lactose not fermented; proteolytic action varies with the species; aerobic and facultatively anaerobic; rarely microaerophilic. *Corynebacterium* is a genus within the family Corynebacteriaceae, order Eubacteriales, and is generally characterized by: straight to slightly curved rods with irregularly stained segments, sometimes granules; frequently show club-shaped swellings; snapping division produces angular and palisade (picket-fence) arrangements of cells; non-motile with exceptions among the plant pathogens; Gram-positive, but sometimes young cells and sometimes old cells losing the stain easily; granules invariably Gram-positive; generally quite aerobic, but microaerophilic or even anaerobic species occur; catalase-positive; may or may not liquefy gelatin; may or may not produce nitrites from nitrates; may or many not ferment sugars, but seldom, if ever, is a high acidity produced; many species oxidize glucose completely to $CO_2$ and $H_2O$ without producing visible gas. *Arthrobacter* is a genus within the family Corynebacteriaceae, order Eubacteriales, and is generally characterized by: in young cultures the cells appear as rods which may vary in size and shape from straight to bent, curved, swollen or club-shaped forms; snapping division may show angular cell arrangement; short filament formation with rudimentary budding may occur, especially in richer liquid media; Gram-negative or Gram-variable, coccoid cells are characteristically observed in cultures and are Gram-negative to Gram-positive; larger coccoid cells which give rise to one or more rod-shaped cells on fresh transfer also occur; generally non-motile; growth on solid media soft or viscous; growth on liquid media generally not profuse; most species liquefy gelatin; little or no acid from carbohydrates; nitrites generally produced from nitrates; indole not produced; aerobic; most species show little or no growth at 37° C. *Microbacterium* is a genus within the family Corynebacteriaceae, order Eubacteriales and is characterized by: small rods with roundel ends; vary in length from 0.5 to 30 microns; non-motile; granulations demonstrable with methylene blue stain; Gram-positive; good surface growth on media supplemented with milk or yeast extract, acid production weak with principally L (+)-actic acid produced from fermented carbohydrates; catalase-positive optimum temperature, 32° C.

Specific non-limiting suitable strains of the genus *Corynebacterium*, in particular of the species *Corynebacterium glutamicum* (*C. glutamicum*), are in particular the known strains as follows:

*Corynebacterium glutamicum* ATCC21608
 *Corynebacterium glutamicum* ATCC13032
 *Corynebacterium acetoglutamicum* ATCC15806
 *Corynebacterium acetoacidophilum* ATCC13870
 *Corynebacterium melassecola* ATCC17965
 *Corynebacterium thermoaminogenes* FERM BP-1539
 *Brevibacterium flavum* ATCC14067
 *Brevibacterium lactofermentum* ATCC13869 and
 *Brevibacterium divaricatum* ATCC14020
  or L-amino acid-producing mutants or strains prepared therefrom.

Microorganisms of the family Enterobacteriaceae selected from the genera *Escherichia, Erwinia, Providencia* and *Serratia* may also be used for the production of amino acids, e.g., methionine, according to the present invention.

Specific useful non-limiting suitable strains of the genus *Escherichia*, in particular those of the species *Escherichia coli* include for example:
 *Escherichia coli* TF427
 *Escherichia coli* H4578
 *Escherichia coli* KY10935
 *Escherichia coli* VNIIgenetika MG442
 *Escherichia coli* VNIIgenetika M1
 *Escherichia coli* VNIIgenetika 472T23
 *Escherichia coli* BKIIM B-3996
 *Escherichia coli* kat 13
 *Escherichia coli* KCCM-10132

Specific non-limiting suitable strains of the genus *Serratia*, in particular of the species *Serratia marcescens* include for example:
 *Serratia marcescens* HNr21
 *Serratia marcescens* TLr156
 *Serratia marcescens* T2000

The methods of mutagenesis, selection and mutant choice have been used to improve the microorganisms for the production of amino acids. For example, strains that are resistant to antimetabolites such as, for example, the lysine analogues of S-(2-aminoethyl)-cysteine or which are auxotrophic for significant regulatory amino acids, and produce L-amino acids, are obtained in this way.

Mutant strains of coryneform glutamic acid-producing bacteria represented by *Corynebacterium glutamicum* which exhibit resistance to analogues of methionine (for example; α-methylmethionine, ethionine, norleucine, N-acetylnorleucine, Trifluoromethylhomocysteine, 2-amino-5-heptenoic acids, 2-amino-4-hexenoic acid, seleno-methionine, methionine sulfoximine, methoxinine, 1-aminocyclopentane carboxylic acid, etc.), are also excellent producers of L-methionine (e.g., as described in U.S. Pat. No. 3,729,381, hereby incorporated by reference in its entirety). Resistance to analogues of methionine can be determined by checking if the mutant can grow in a medium containing 500 µg/ml of an analogue though the concentration varies depending upon the microorganisms and the analogues. It can be generally stated that the following L-glutamic acid-producing microorganisms are preferred in connection with the process of the present invention: *Brevibacterium glutamigenum, Brevibacterium lactoferinentum, Brevibacterium saccharolyficum, Brevibacterium thiogenitalls, Brevibacterium* sp., *Corynebacterium* sp., *Corynebacterium callunae, Corynebacterium acetoacidophilum, Corynebacterium glutamicum, Corynebacterium melassecola, Microbacteriumflavum,* var. *glutamicum, Arthrobacter* sp. A particularly preferred mutant strain of *Corynebacterium glutamicum* has been deposited with the American Type Culture Collection, Rockville, Md., and has been accorded accession number ATCC 21608.

Recombinant DNA techniques can be used for strain-improvement for the production of amino acids (e.g., see U.S. Pat. No. 4,278,765, hereby incorporated by reference in its entirety). Reference is made to standard textbooks of molecular biology that contain definitions and methods and means for carrying out basic recombinant DNA techniques, encompassed by the present invention. See, for example, Maniatis et al., Molecular Cloning: A Laboratory Manual, Cold Spring Harbor Laboratory, New York (1982) and Sambrook et al., Molecular Cloning: A Laboratory Manual, Cold Spring Harbor Laboratory, New York (1989), hereby incorporated by reference in their entirety.

For example, L-amino acid producing strains of *Corynebacterium glutamicum* can be improved by transformation of individual amino acid biosynthetic genes. Review articles about this topic can be found, inter alia, in Kinoshita ("Glutamic Acid Bacteria", in: Biology of Industrial Microorganisms, Demain and Solomon (Eds.), Benjamin Cummings, London, UK, 1985, 115-142), Hilliger (BioTec 2, 40-44 (1991)), Eggeling (Amino Acids 6, 261-272 (1994)), Jetten and Sinskey (Critical Reviews in Biotechnology 15, 73-103 (1995)) and Sham et al. (Annuals of the New York Academy of Science 782, 25-39 (1996)), incorporated by reference in their entirety.

For methionine production, genes encoding methionine biosynthetic pathway can be transformed into desired bacteria e.g., *Corynebacterium glutamicum*. Such genes are known in the art, for example, as described in U.S. patent applications 2003/0,092,026A1 (metD); 2002/0,110,878A1 (metY); 2002/0,110,877A1 (metE); 2002/0,102,664A1 (metR and metZ); 2002/0,049,305A1 (metF); 2002/0,048,793A1 (metH), each of the patent applications is hereby incorporated in its entirety.

To increase the production of methionine from recombinant bacteria, the copy number of the corresponding gene can be increased or the promoter and regulation region or the ribosome bonding site, which are located upstream of the coding sequence, can be mutated. Expression cassettes, which are incorporated upstream of the coding sequence, operate in the same way.

It is also possible to increase expression during the course of fermentative methionine production with inducible promoters. Expression is also improved by measures aimed at prolonging the lifetime of m-RNA. Furthermore, enzyme activity can also be amplified by inhibiting degradation of the enzyme protein. The genes or gene constructs can either be present in plasmids with different copy numbers or be integrated and amplified in the chromosome. Alternatively, overexpression of the genes concerned can also be achieved by modifying the composition of the media and management of the culture.

Instructions for these procedures can be found by a person skilled in the art in, inter alia, Martin et al. (Bio/Technology 5, 137-146 (1987)), in Guerrero et al. (Gene 138, 35-41 (1994)), Tsuchiya and Morinaga (Bio/Technology 6, 428-430 (1988), in Eikmanns et al. (Gene 102, 93-98 (1991)), in European Patent EP-B 0 472 869, in U.S. Pat. No. 4,601,893, in Schwarzer and Puhler (Bio/Technology 9, 84-87 (1991), in Reinscheid et al. (Applied and Environmental Microbiology 60, 126-132 (1994)), in LaBarre et al. (Journal of Bacteriology 175, 1001-1007 (1993)), in Patent Application WO 96/15246, in Malumbres et al. (Gene 134, 15-24 (1993)), in Japanese Patent JP-A-10-229891, in Jensen and Hammer (Biotechnology and Bioengineering 58, 191-195 (1998)), in Makrides (Microbiological Reviews 60:512-538 (1996)) and in well-known textbooks relating to genetics and molecular biology, each of which is hereby incorporated by reference in its entirety.

In an preferred embodiment, L-methionine is produced by culturing in a nutrient medium an L-methionine-producing certain type mutant strain of coryneform glutamic acid producing bacteria represented by *Corynebacterium glutamicum*, accumulating L-methionine in the culture liquor and recovering L-methionine therefrom.

Fermentation

Culturing and fermentation of the suitable amino acid producing bacteria can be performed according to any method known in the art, e.g., as described in U.S. patent application Nos. 2003/0,092,026A1; 2002/0,142,405A1; U.S. Pat. No. 3,546,071, hereby incorporated by reference in their entirety.

The culture medium to be used must meet the requirements of the particular strains in a suitable manner. Descriptions of culture media for various microorganisms are contained in the handbook "Manual of Methods for General Bacteriology" of the American Society for Bacteriology (Washington D.C., USA, 1981).

The culture medium employed in the present invention can be either synthetic or natural, so long as the medium properly contains a carbon source, a nitrogen source, inorganic compounds and small amounts of additional nutrients necessary for the specific microorganism used. Other than the above, there are no special restrictions attached to other essentials of the medium composition.

The following substances can be used individually, or as a mixture, as the source of carbon:
(a) sugars and carbohydrates, such as e.g. glucose, sucrose, lactose, fructose, maltose, molasses, starch and cellulose,
(b) oils and fats, such as, soy oil, sunflower oil, groundnut oil and coconut fat,
(c) fatty acids, such as palmitic acid, stearic acid and linoleic acid,
(d) alcohols, such as glycerol and ethanol, and
(e) organic acids, such as acetic acid, pyruvic acid, fumaric acid, lactic acid.

The following substances can be used individually, or as a mixture, as the source of nitrogen:
(a) Organic nitrogen-containing compounds, such as peptones, yeast extract, meat extract, malt extract, corn steep liquor, soya bean flour and urea, or
(b) inorganic compounds, such as ammonium sulfate, ammonium chloride, ammonium phosphate, ammonium carbonate and ammonium nitrate, The following sources can be used individually, or as a mixture, as the source of phosphorus:
Phosphoric acid, potassium dihydrogen phosphate or dipotassium hydrogen phosphate or the corresponding sodium-containing salts.

The culture medium must furthermore comprise salts of metals, such as magnesium sulfate or iron sulfate, which are necessary for growth.

Essential growth substances, such as amino acids and vitamins, can be employed in addition to the above-mentioned substances. Suitable precursors can moreover be added to the culture medium. The starting substances mentioned can be added to the culture in the form of a single batch, or can be fed in during the culture in a suitable manner.

Acid compounds, such as an inorganic acid, e.g., hydrochloric acid, hydrobromic acid, sulfuric acid, phosphoric acid, hydrogen bromide, etc. or an organic acid, e.g., formic acid, acetic acid, propionic acid, trichloroacetic acid, trifluoroacetic acid, etc., can be added into the fermentation medium in a suitable manner, e.g., either manually or mechanically, to control the pH of the culture, and to increase solubility of methionine in the fermentation medium.

Antifoams, such as, for example, fatty acid polyglycol esters, can be employed to control the development of foam. Suitable substances having a selective action, such as, for example, antibiotics, can be added to the medium to maintain the stability of plasmids if recombinant bacteria stains are used. To maintain aerobic conditions, oxygen or oxygen-containing gas mixtures, such as air, are introduced into the culture. The temperature of the culture is usually between 20° C. to 45° C., and preferably between 25° C. to 40° C. Culturing is continued until a maximum of the desired product has formed. This target is usually reached within 10 hours to 160 hours.

In one embodiment, the microorganism is grown in a seed medium prior to being used for inoculation of the culture medium. The seed medium is incubated under favorable growth conditions for a period of time sufficient to develop a suitable organism population, typically for about 24 hours. The seed medium is then used to inoculate the culture medium. Fermentation is then carried out until a considerable amount of L-methionine is produced and accumulated in the resultant medium, usually 1 to 5 days. After the completion of culturing, the L-methionine is readily recovered from the medium by separating the medium from the cells and subjecting the cell free medium to an ion exchange resin treatment or the like.

Post Fermentation

The fermentation broth prepared in this manner, in particular containing methionine, is then further processed. Depending on requirements, all or some of the biomass can be removed from the fermentation broth by separation methods. The removal of biomass may be particularly important to make a cell free preparation for animal feed when certain host (e.g., E. coli) is used. Examples of such separation methods are centrifugation, filtration, decanting or a combination thereof. Alternatively, the biomass can be left completely in the fermentation broth. This broth can optionally be thickened or concentrated by known methods. Examples of such thickening or concentrating methods include conventional methods such as evaporation, reverse osmosis, or by nanofiltration. Examples of instruments that can be used in evaporation processes include methods a rotary evaporator, thin film evaporator, and falling film evaporator. This thickened or concentrated fermentation broth can then be worked up. Examples of methods used to work up the thickened or concentrated fermentation broth include freeze drying, spray drying, spray granulation or by other processes. Optionally, the fermentation broth can be worked up to yield a preferably free-flowing, finely divided powder.

In an alternative embodiment, the starting point for making a methionine preparation can be the insoluble material collected from the fermentation broth. Because of the inherently low solubility of methionine in aqueous solutions, a great proportion of the methionine produced by the microorganism often exists in the insoluble state. Therefore, collection of insoluble material following fermentation by filtration or centrifugation can serve as the starting point for making the methionine preparation.

To increase recovery of methionine in the insoluble phase, the pH of the fermentation broth can be adjusted to further reduce its solubility. The temperature of the fermentation broth may additionally be reduced, for example, to less than 20° C., typically less than 10° C., less than 6° C. or less than 4° C. Using insoluble material as the starting point for making a methionine preparation is especially advantageous in situations where large volumes of fermentation broth is processed: due to the abundance of insoluble methionine, collecting the insoluble material serves as a significant enrichment step. The collected insoluble material may be resuspended in water or a solution. The choice of solution depends on the ideal conditions for ensuring that the microorganism remains relatively intact. Factors to consider include osmolarity, the presence of monovalent and divalent cations to maintain integrity of the cell wall, and the absence of compounds with detergent-like properties, which can disrupt the cell membrane and release the intracellular contents of the microorganism. In addition, it is preferable that the solution not possess strong pH buffering capacity that may interfere with altering the pH to increase the solubility of methionine.

To solubilize methionine, either from a fermentation broth or insoluble material resuspended in solution, the temperature of the solution can be increased to at least 40° C. to increase the solubility of methionine within the fermentation broth. In one embodiment, the temperature of the fermentation broth is raised to at least 50° C. In another embodiment, the temperature of the fermentation broth is raised to at least 60° C. In yet another embodiment, the temperature of the fermentation broth is raised to at least 70° C.

If it is desirable to remove the biomass, some or all of the biomass can be removed from the fermentation broth by separation methods such as filtration or centrifugation. The biomass is preferably removed while the temperature is increased (i.e., when the solubility of methionine is increased) to reduce the loss of insoluble methionine during this step.

Alternatively, or in addition to increasing the temperature of the fermentation broth, an acid compound can be added into the fermentation broth in a suitable manner, e.g., either manually or mechanically, at the end of the fermentation, but before the optional removal of the biomass, an acid compound can be added into the fermentation broth in a suitable manner, e.g., either manually or mechanically, to control the pH of the broth and to increase the solubility of methionine within the broth.

In one embodiment, a pH of 4.0 or below is achieved for the fermentation broth to increase the solubility of methionine. In another embodiment, a pH of 3.5 or below is achieved for the fermentation broth to increase the solubility of methionine. In another embodiment, a pH of 3.0 or below is achieved for the fermentation broth to increase the solubility of methionine.

As previously stated, the adjustment of pH to an acidic pH can be performed in combination with increasing the temperature of the fermentation broth to at least 40° C. For example, the pH of the fermentation broth can be adjusted to an acidic pH of 3.0, and the temperature of the fermentation broth increased to 50° C. pH can be measured with or without the removal of any biomass according to the present invention.

The solubility of methionine in an acidified such fermentation medium or fermentation broth (25° C.) is at least 40.57 g/L, for example, at least 47.33 g/L, 50.72 g/L, 54.10 g/L, 57.48 g/L, 60.86 g/L, 64.24 g/L, 67.62 g/L, 101.43 g/L, 135.24 g/L, 169.05 g/L or more.

Optionally, the acidified broth (i.e., the broth with an acidic pH) can be used for further purification of methionine by ion exchange methods known in the art, e.g., as described in Spackman et al. (1958, Analytical Chemistry, 30: 1190), U.S. patent applications 2002/0,110,877A1 and 2003/0,045, 753A1, each of which is hereby incorporated by reference in its entirety.

When ion exchange is used, the acidified broth is passed over a cationic ion column to separate the methionine from the other broth constituent (e.g., the biomass). The bound methionine is then eluted from the column with ammonium hydroxide (or any other base). The ammonia can then be stripped from methionine to make methionine free base to make a purified methionine preparation.

Alternatively, the acid compound can be added after the removal of biomass, but before thickening or concentrating. This is useful if the methionine solubility at the end of the fermentation is below the solubility at a neutral pH.

In some embodiments of the invention, it is preferred to adjust the pH of the broth back to pH 2.5-7, preferably, pH 3.5-7, more preferably, 5-7, before drying to make the preparation more suitable for animal feeding.

As an alternative to adding an acid compound, basic compounds, such as sodium hydroxide, potassium hydroxide, ammonia or aqueous ammonia, ammonium hydrochloride, ammonium sulfate can be added into the fermentation broth in a suitable manner, e.g., either manually or mechanically, at the end of the fermentation, but before the optional removal of the biomass, to control the pH of the broth and to increase the solubility of methionine. In one embodiment, the pH of the broth is increased to at least 8.5. In another embodiment, the pH is increased to at least 9.0. In yet another embodiment, the pH is increased to at least 9.5. In still another embodiment, the pH is increased to at least 10.0. Similar to the embodiments involving acid addition, the adjustment of pH to a basic pH can be performed in combination with increasing the temperature of the fermentation broth to at least 40° C. For example, the pH of the fermentation broth can be adjusted to a basic pH of 8.5, and the temperature of the fermentation broth increased to 70° C.

Alternatively, the base can be added after the removal of biomass, but before thickening or concentrating. This is useful if the methionine solubility at the end of the fermentation is below the solubility at a neutral pH.

In one embodiment, a liquid sodium methionate or ammonium methionate product is obtained.

Once the insoluble material (containing whole cells) is removed from the methionine preparation, additional steps of methionine purification can be performed. The methionine preparation can be decolorized using absorbents such as activated carbon, for example the Darco KB and KB-B activated carbon (American Norit Co, Buford, Ga.). The absorbent can simply be mixed with the methionine preparation at a range of about 1-15 g/L of methionine preparation and stirred, with optional heating to between 40° C. and 70° C., for 1 to 24 hrs. The activated carbon can then be removed by simple filtration.

In another embodiment, a purified methionine preparation that is essentially cell free is obtained by taking the ammonium methionate salt solution which is at high pH to strip off the ammonia. The methionate solution can then be concentrated and crystallized to effectively produce a purified methionine preparation, for example, as described for a chemically-produced ammonium methionate solution in U.S. Pat. No. 6,417,395 (the entirety of which is hereby incorporated by reference). Prior to crystallization, the methionine preparation can be further concentrated, as described above, in order increase recovery. Crystallization of methionine can also be achieved by a number of means, for example by addition of aluminum salts of organic acids as is described in U.S. Pat. No. 5,463,120, by addition of alcohols, phenols or ketones as described in Japanese Patent published under JP 68-024890, or by addition of anionic or non-ionic surface active agents, as disclosed in Japanese Patent published under JP 71-019610. The three patents mentioned above are hereby incorporated in their entirety by reference. Crystallization of methionine can also be achieved by adjusting the pH of the methionine preparation to pH 5.74, the isoelectric point of methionine, and reducing the temperature to below 10° C., typically less than or equal to 4° C. and permitting the crystals to form for at least 3 hrs, typically overnight. Methionine crystals can be collected, for example, by filtration or centrifugation directly from the chilled solution, or after allowing the solution to warm to room temperature.

Both the collected crystals and the remaining solution can be analyzed for purity of methionine. Purity can be analyzed by any number of means to determine the methionine content of the crystal and the solution, including HPLC. If a significant amount of methionine remains in solution (in the mother liquor), then crystallization can be repeated. If needed, the crystals can be redissolved, and crystallization repeated in order to increase purity.

The free-flowing, finely divided powder can be converted by suitable compacting or granulating processes, e.g., as described in U.S. patent application Nos. 2003/0,092,026A1 and 2003/0,059,903A1, the entirety of each is hereby incorporated by reference. Preferably, the powder can be converted into a coarse-grained, readily free-flowing, storable and largely dust-free product. During granulation or compaction, it is advantageous to employ conventional organic or inorganic auxiliary substances or carriers. Examples of such organic or inorganic auxiliary substances or carriers include starch, gelatin, cellulose derivatives or similar substances. Further, these substances can be used as binders, gelling agents or thickeners in foodstuffs or feedstuffs processing. Further examples of these substances include silicas, silicates or stearates.

Alternatively, the product can be absorbed onto an organic or inorganic carrier substance that is known and conventional in feedstuffs processing. Examples of such organic or inorganic carrier substances include silicas, silicates, grits, brans, meals, starches, sugars or others. Further, the product simultaneously or subsequently mixed and/or stabilized with conventional thickeners and/or binders.

Finally, the product can be brought into a state in which it is stable to digestion by animal stomachs, in particular the stomach of ruminants, by coating processes, i.e. coating. Examples of such conventional coating processes include those that use film-forming agents. Examples of film-forming agents include metal carbonates, silicas, silicates, alginates, stearates, starches, gums and cellulose ethers.

If the biomass (i.e., insoluble material) is separated from methionine during the preparation, further inorganic solids which can be optionally added during the fermentation can be optionally removed. In addition, organic substances can be optionally formed and/or added and are optionally present in solution in the fermentation broth.

Examples of the above-mentioned organic substances include organic by-products. Organic by-products can be optionally produced, in addition to the L-methionine, and can be optionally discharged by the microorganisms employed in the fermentation. Examples of organic by-products include L-amino acids chosen from the group consisting of L-valine, L-threonine, L-alanine or L-tryptophan. Further examples of organic by-products include vitamins chosen from the group consisting of vitamin B1 (thiamine), vitamin B2 (riboflavin), vitamin B5 (pantothenic acid), vitamin B6 (pyridoxine), vitamin B12 (cyanobalamin), nicotinic acid/nicotinamide and vitamin E (tocopherol). Even further examples of organic by-products include organic acids. Examples of organic acids are those that contain one to three carboxyl groups. Examples of organic acids containing one to three carboxyl groups include acetic acid, lactic acid, citric acid, malic acid and/or fumaric acid. Finally, Examples of organic by-products include sugars. Examples of sugars include such trehalose. These compounds are optionally desired if they improve the nutritional value of the product.

Purified organic substances, including methionine (e.g., L, D, or D/L methionine) or methionine esters or the hydroxy analog of methionine (e.g., 2-hydroxy-4-(methylthio)butanoic acid, provided by Novus International, St. Louis, Mo., USA) can also be added into the fermentation medium or broth, e.g., during a suitable process step (e.g., into the fermentation medium or the fermentation broth, or concentrated fermentation broth, or the dry methionine preparation). The addition of such material increases the methionine content of the methionine preparation.

Such organic substances can be in many forms. Examples of such forms include concentrate and/or pure substance in solid and/or liquid form. These organic substances mentioned can optionally be added individually or as mixtures to the resulting or concentrated fermentation broth, or also optionally during the drying or granulation process. It is likewise possible to optionally add an organic substance or a mixture of several organic substances to the fermentation broth and also to add further organic substances or a mixture of several organic substances during a later process step. Examples of such as later step can include a granulation step.

In one aspect of the invention, the biomass can be separated from methionine to the extent of up to 70%, preferably up to 80%, preferably up to 90%, preferably up to 95%, and particularly preferably up to 100%.

In another aspect of the invention, less than 20% of the biomass, preferably less than 15%, preferably less than 10%, preferably less than 5%, particularly preferably no biomass is separated from methionine.

The methionine preparation made in the present invention can be used as a feed additive for animal nutrition. Alternatively, the fermentation broth obtained after culturing a methionine-producing microorganism can be used as a feed additive.

The L-methionine content of the animal feed additive is conventionally 1% per weight to 80% per weight, preferably 2% per weight to 80% per weight, particularly preferably 4% per weight to 80% per weight, and very particularly preferably 8% per weight to 80% per weight, based on the dry weight of the animal feed additive. Contents of 1% per weight to 60% per weight, 2% per weight to 60% per weight, 4% per weight to 60% per weight, 6% per weight to 60% per weight, 1% per weight to 40% per weight, 2% per weight to 40% per weight or 4% per weight to 40% per weight are likewise possible. The ranges for content of the animal feed additive include all specific values and subranges therebetween, such 2, 4, 6, 8, 10, 15, 20, 25, 30, 35, 40, 45, 50, 55, 60, 65, 70, and 75% per weight. The water content of the feed additive is conventionally up to 5% per weight, preferably up to 4% per weight, and particularly preferably less than 2% per weight.

An animal feed additive according to the present invention can comprise 1% per weight to 80% per weight L-methionine, D-methionine, D, L-methionine, or a mixture thereof with 1 to 40% per weight of a second amino acid, e.g., L-lysine, D-lysine or D,L-lysine, or several second amino acids, based on the dry weight of the animal feedstuffs additive. The ranges for content of L-methionine, D-methionine, D,L-methionine, or a mixture thereof with the second amino acid in the animal feedstuffs additive include all specific values and subranges therebetween, such 2, 4, 6, 8, 10, 15, 20, 25, 30, 35, 40, 45, 50, 55, 60, 65, 70, and 75% per weight. The ranges for content of the second amino acid, e.g., L-lysine, D-lysine or D, L-lysine in the mixture with L-methionine, D-methionine, D,L-methionine in the animal feedstuffs additive include all specific values and subranges therebetween, such 2, 4, 6, 8, 10, 10 15, 20, 25, 30, and 35% per weight.

Drying

It is one object of the present invention to provide a dried methionine preparation. The present method of making a methionine preparation thus can further comprise a drying step as described herein above.

Practice of certain specific embodiments of the invention is illustrated by the following representative examples.

EXAMPLES

Example 1

Culturing Methionine Producing Microorganisms in Fermentation Medium

Methionine producing bacteria *Corynebacterium glutamicum*—ATCC21608, obtained from American Type Culture Collection, was aseptically added to 5 mL of nutrient broth (DIFCO) and allowed to grow for 24 hours at 30° C. under vigorous shaking. After the 24 hour incubation, the culture was used to seed 100 ml of nutrient broth (DIFCO) and allowed to grow for an additional 18 hours at 30° C. under vigorous shaking. Aliquots of the bacteria were then transferred to nutrient agar plates and the plates placed in an incubator for 24 hours. The plates were examined for growth and were refrigerated until further use.

Colonies from agar plates were aseptically transferred into 250 mL flasks containing 30 ml of nutrient broth (DIFCO) and allowed to grow at 30° C. After 24 hours of growth, these microorganisms were used as seed culture in a 3-L fermenter containing growth media consisting of 50 g/L glucose, 50 g/L soy protein hydrolyzate, 1 g/L $K_2HPO_4$, 45 g/L $(NH_4)_2SO_4$, 400 mg/L $MgSO_4.7H_2O$, 10 mg/L $MnSO_4.4H_2O$, 0.2 mg/L thiamin HCl and 0.05 mg/L biotin. Fermentation was carried out at 31° C. under vigorous agitation and good aeration. pH was maintained at 7.45 during fermentation by addition of ammonium hydroxide ($NH_4OH$). The organisms grew quite well under these conditions with a typical optical density (as measured as $OD_{600}$) in the range of 25 to 30 after only 24 hours. Fermentation batches were terminated once the initial glucose charge was consumed. The residual L-methionine produced during these fermentations was supplemented with additional L-methionine as described in the Examples below.

Example 2

Increased Recovery of L-Methionine at Basic pH

The fermentation broth produced by growing *Corynebacterium glutamicum*—ATCC 21608, as discussed in Example 1, was supplemented with L-methionine to give a final methionine concentration of 75.2 g/L in the slurry. The resulting slurry consists of soluble and insoluble L-methionine, microbial cells and constituents of fermentation media. The pH of the slurry was measured to be 5.54. A well-mixed sample of this slurry was drawn, and solids removed from the sample by centrifugation followed by filtration. The concentration of methionine in the filtrate of the slurry was determined by HPLC to be 38 g/L, giving a concentration of soluble methionine in a typical fermentation broth.

To the remaining slurry, a 50% solution of sodium hydroxide (NaOH) was added at a level corresponding to 1 equivalent weight of L-methionine, raising its pH to 9.36. From a well-mixed sample of this slurry, solids were removed as before by centrifugation and filtration. Soluble methionine concentration in the filtrate was 78 g/L. The difference with the concentration in a typical fermentation broth represents an increase in solubility of methionine in the slurry due to the addition of NaOH. NaOH concentration was further increased in the slurry to 2 equivalent weight of L-methionine, which raised the pH to 10.22. At this stage the solubility of methionine in the solution was unchanged. The pH of the slurry was raised to 12.53 by increasing the concentration of NaOH to 2.5 equivalent weight L-methionine. This did not further increase the solubility of L-methionine. At this point, the whole cells were separated from the methionine and fermentation solubles by centrifugation.

To the cell free broth containing the solubilized L-methionine, sulfuric acid (96% w/w) was added and its pH lowered to 5.95, the isoelectric point of L-methionine. At this pH, the methionine molecule does not have any charge, and results in the formation of methionine crystals. The slurry was then stored overnight at 4° C. to allow for precipitation of the crystals. The slurry was then centrifuged to collect the methionine crystals. The concentration of methionine remaining in the supernatant was found to be 33 g/L. The collected crystals were dried in a lyophilizer. The overall recovery of methionine using this of the process was 73%.

Example 3

Increased Recovery of L-Methionine at Basic pH

Methionine was added to the fermentation broth at a concentration of 56 g/L. In addition to soluble methionine, the slurry had insoluble methionine, microbial cells and components of fermentation media. 50% NaOH was added to the slurry at a concentration equal to 0.5 eq. weight of methionine. The pH of the slurry after addition of NaOH was 8.92 and the soluble methionine concentration in it was 58 g/L. Additional NaOH was added to the slurry to 1 eq weight of L-methionine, raising the pH of the slurry to 9.38. A sample of the slurry was removed and filtered as previously described. The concentration of methionine in the filtrate was found to be 56 g/L. No additional methionine was solubilized by increasing the concentration of NaOH to 1.5, 2 and 2.5 eq wt of methionine. The pH of the slurry was 9.82, 10.47 and 12.23 after addition of NaOH of 1.5, 2 and 2.5 eq wt of methionine, respectively.

Example 4

Increased Recovery of L-Methionine at Elevated Temperatures

Methionine was added to fermentation broth at a concentration of 77 g/L. The slurry was then heated to 70° C. without pH adjustment. This slurry was then filtered through a 0.45 micron filter in a heated filtration unit to remove the whole cells and other insoluble fermentation broth components. The filtrate was collected and analyzed for methionine. The concentration of methionine in the filtrate was 74.6 g/L. Thus, by raising the temperature of L-methionine containing fermentation broth from 22° C. to 70° C. increased the solubility of methionine from 38 g/L to 74.6 g/L. The filtrate was subsequently cooled to crystallize the free methionine. The methionine crystals were freeze-dried to remove residual moisture.

Example 5

Increased Recovery of L-Methionine at Acidic pH

The following examples demonstrate the use of an acid to increase the solubility of methionine.

A slurry containing 75 g/L of methionine was prepared by supplementing the fermentation broth produced with L-methionine as previously described.

Concentrated sulfuric acid ($H_2SO_4$, 96% w/w) was added in a concentration equal to 1 equivalent weight of methionine to the slurry, lowering the pH of the slurry to 2.49. Methionine concentration was measured from a sample after centrifugation and filtration as previously described. The concentration of soluble methionine increased to 75 g/L. Further addition of $H_2SO_4$ at 1.5 and 2 equivalents did not cause additional increase in the solubility of methionine in the fermentation broth. The pH of the slurry was 1.93 at 1.5 eq $H_2SO_4$ and 1.68 at 2 eq $H_2SO_4$.

At pH of 1.68, cells from the slurried fermenter broth were separated first by centrifugation followed by filtration through a 0.45 micron filter. The pH of the filtrate was then raised to 5.75, the isoelectric point of methionine by addition of 50% NaOH, resulting in formation of L-methionine crystals. The slurry was placed in a refrigerator at 4° C. for 18 hours to allow for additional crystallization of methionine. The crystals were then removed by centrifugation and filtration and further dried on a lyophilizer. The dried crystals were harvested from the lyophilizer. The concentration of methionine remaining in the supernatant (mother liquor) was 47.2 g/L. To recover additional methionine, the mother liquor was then placed in the refrigerator overnight. Crystals were collected by centrifugation at 4° C. by using a pre-chilled centrifuge. As a result of lower temperature, additional L-methionine was crystallized and recovered.

Example 6

Increased Recovery of L-Methionine at Acidic pH

L-methionine was added to fermentation broth at a final concentration of 55 g L-methionine per liter of the broth (55 g/L) as determined by HPLC. $H_2SO_4$ (96% w/w) at a concentration of 1 equivalent weight of methionine was added to this slurry, decreasing the pH of the broth to 2.39. The solubility of methionine in the broth at this pH was found to be 55 g/L, by measuring a sample which was centrifuged and filtered to remove insoluble material as previously described. Adding more $H_2SO_4$ to the broth at 1.5 and 2 times the equivalent weight to L-methionine further lowered the pH of the broth to 2.09 and 1.74 respectively, but did not result in further recovery of methionine.

For optimal recovery of methionine, solids from the acidified slurry above were removed by centrifugation and filtration and the pH of the recovered filtrate was raised to 5.6 using NaOH. Cooling the slurry to 4° C. for 18 hours resulted in formation of crystals in the solution. The concentration of methionine remaining in the supernatant (mother liquor) was 39.5 g/liter. This solution was placed again in the refrigerator at 4° C. for 18 hours to allow for formation of additional methionine crystals. Crystals formed after 18 hours at 4° C. were filtered and dried in a lyophilizer.

OTHER EMBODIMENTS

The foregoing examples demonstrate experiments performed and contemplated by the present inventors in making and carrying out the invention. It is believed that these examples include a disclosure of techniques which serve to both apprise the art of the practice of the invention and to demonstrate its usefulness. It will be appreciated by those of skill in the art that the techniques and embodiments disclosed herein are preferred embodiments only that in general numerous equivalent methods and techniques may be employed to achieve the same result.

All of the references identified hereinabove, are hereby expressly incorporated herein by reference to the extent that they describe, set forth, provide a basis for or enable compositions and/or methods which may be important to the practice of one or more embodiments of the present inventions.

The invention claimed is:

1. A method of making a methionine preparation comprising:
   (a) culturing a methionine-producing microorganism in a fermentation medium to yield a fermentation broth;
   (b) solubilizing methionine in said fermentation broth by raising the pH 8.5 or above, or lowering the pH to 3.5 or below;
   (c) removing insoluble material from said fermentation broth to yield a clarified broth;
   (d) crystallizing methionine from said clarified broth; and,
   (e) isolating the methionine crystals to produce a methionine preparation.

2. The method of claim 1, wherein said base is selected from the group consisting of sodium hydroxide, potassium hydroxide and ammonium hydroxide.

3. The method of claim 1, wherein temperature of said fermentation broth is increased to at least 40° C. prior to removal of said insoluble material.

4. The method of claim 1, wherein temperature of said methionine-enriched broth to at least 40° C.

5. A method of making a methionine preparation comprising:
   (a) culturing a methionine-producing microorganism in a fermentation medium to yield a fermentation broth;
   (b) solubilizing methionine in said fermentation broth by raising the temperature of the broth to at least 40° C.;
   (c) removing insoluble material from said fermentation broth to yield a methionine-enriched clarified broth;
   (d) crystallizing methionine from said clarified broth; and,
   (e) isolating the methionine crystals to produce a methionine preparation.

6. The method of claim 5, wherein said solubilizing further comprises raising the pH 8.5 or above, or lowering the pH to 3.5 or below.

7. The method of claim 5, wherein a methionine preparation is made by drying said clarified broth.

8. A method of making a methionine preparation comprising:
   (a) culturing a methionine-producing microorganism in a fermentation medium to produce a fermentation broth;
   (b) collecting methionine-enriched insoluble material from said fermentation broth;
   (c) solubilizing methionine from said methionine-enriched insoluble material by addition of an acid to lower the pH to 3.5 or below, or a base to raise the pH to 8.5 or above to produce a methionine-enriched broth;
   (d) crystallizing methionine from said methionine-enriched broth; and,
   (e) isolating the methionine crystals to produce a methionine preparation.

9. A method of making a methionine preparation comprising:
   (a) culturing a methionine-producing microorganism in a fermentation medium;
   (b) obtaining a methionine-containing fermentation broth from said culturing, wherein the pH of said fermentation broth is adjusted to an acidic pH or basic pH; and
   (c) concentrating said methionine-containing fermentation broth and optionally drying to produce a methionine preparation.

10. A method of making a methionine preparation comprising:
   (a) culturing a methionine-producing microorganism in a fermentation medium;
   (b) obtaining a methionine-containing fermentation broth from said culturing, wherein the pH of said fermentation broth is adjusted to an acidic pH or basic pH; and
   (c) removing from said methionine-containing fermentation broth to produce a methionine preparation.

* * * * *

UNITED STATES PATENT AND TRADEMARK OFFICE
CERTIFICATE OF CORRECTION

PATENT NO. : 8,338,141 B2  
APPLICATION NO. : 10/886863  
DATED : December 25, 2012  
INVENTOR(S) : Steve Lorbert et al.

Page 1 of 1

It is certified that error appears in the above-identified patent and that said Letters Patent is hereby corrected as shown below:

In the Claims

Column 23, Claim 4, line 2, after the word "broth" and before "to", insert the following:
--is increased--

Column 24, Claim 6, line 2, after the word "pH" and before "8.5", insert the following: --to--

Signed and Sealed this  
Eighth Day of April, 2014

Michelle K. Lee  
*Deputy Director of the United States Patent and Trademark Office*

UNITED STATES PATENT AND TRADEMARK OFFICE
CERTIFICATE OF CORRECTION

PATENT NO. : 8,338,141 B2
APPLICATION NO. : 10/886863
DATED : December 25, 2012
INVENTOR(S) : Steve Lorbert et al.

Page 1 of 1

It is certified that error appears in the above-identified patent and that said Letters Patent is hereby corrected as shown below:

In the Claims

Column 23, Claim 4, line 27, after the word "broth" and before "to", insert the following:
--is increased--

Column 24, Claim 6, line 2, after the word "pH" and before "8.5", insert the following: --to--

This certificate supersedes the Certificate of Correction issued April 8, 2014.

Signed and Sealed this
Sixth Day of May, 2014

Michelle K. Lee
*Deputy Director of the United States Patent and Trademark Office*